US012626017B2

(12) United States Patent
Chinnathambu et al.

(10) Patent No.: US 12,626,017 B2
(45) Date of Patent: May 12, 2026

(54) SYSTEMS AND METHODS FOR DE-IDENTIFYING HEALTHCARE DATA IN A HEALTH ANALYSIS PLATFORM

(71) Applicant: Medidata Solutions, Inc., New York, NY (US)

(72) Inventors: Krishnamoorthy Chinnathambu, Iselin, NJ (US); Bhargav Koduru, Boston, MA (US); Luke Morgan, Cincinnati, OH (US); Trey Moore, Henrico, VA (US)

(73) Assignee: Medidata Solutions, Inc., New York, NY (US)

( * ) Notice: Subject to any disclaimer, the term of this patent is extended or adjusted under 35 U.S.C. 154(b) by 47 days.

(21) Appl. No.: 18/919,639

(22) Filed: Oct. 18, 2024

(65) Prior Publication Data

US 2026/0111603 A1     Apr. 23, 2026

(51) Int. Cl.
G06F 21/62     (2013.01)
G16H 10/20     (2018.01)

(52) U.S. Cl.
CPC ......... *G06F 21/6254* (2013.01); *G16H 10/20* (2018.01)

(58) Field of Classification Search
CPC ............................ G06F 21/6254; G16H 10/20
See application file for complete search history.

(56) References Cited

U.S. PATENT DOCUMENTS

| | | | |
|---|---|---|---|
| 2002/0002474 A1* | 1/2002 | Michelson ............. | G16H 10/60 705/3 |
| 2005/0075832 A1* | 4/2005 | Ikeguchi ................ | G16H 70/20 702/179 |
| 2012/0101843 A1* | 4/2012 | Mathur .................. | G06Q 40/08 705/2 |
| 2022/0157412 A1* | 5/2022 | Ikeda ..................... | G16H 40/20 |

OTHER PUBLICATIONS

Yuvaraj et al., "An Optimal Attribute-Focused Privacy-Preserving Anonymization Scheme for Healthcare Data in Cloud Systems", Sep. 2023, 4th International Conference on Smart Electronics and Communication, pp. 1753-1758 (Year: 2023).*

(Continued)

*Primary Examiner* — Kenneth W Chang
(74) *Attorney, Agent, or Firm* — Fish & Richardson P.C.

(57) ABSTRACT

Systems and methods for improving data security in a computerized health analysis platform are disclosed. For instance, a method includes (i) reading clinical study data sets regarding one or more clinical studies from a hardware storage device, (ii) executing a first computer executable de-identification function with respect to direct identifiers included in each of the clinical study data sets to generate modified clinical study data sets, (iii) generating a standardized data set based on the modified clinical study data sets, (iv) executing a second computer-executable de-identification function with respect to clinical study information portion included in the standardized data set to generate a modified standardized data set, (v) generating a first data structure representing the modified standardized data set, and (vi) storing the first data structure in the hardware storage device.

20 Claims, 5 Drawing Sheets

(56)                     References Cited

OTHER PUBLICATIONS

Carmona et al., "Towards the Analysis of How Anonymization Affects Usefulness of Health Data in the Context of Machine Learning", Jun. 2019, IEEE 32nd International Symposium on Computer-Based Medical Systems, pp. 604-608 (Year: 2019).* cdisc.org [online], "ADaM," available on or before Nov. 20, 2021, via Internet Archive: Wayback Machine URL <https://web.archive.org/web/20211120111553/https://www.cdisc.org/standards/foundational/adam>, retrieved on Mar. 19, 2025, retrieved from URL <https://www.cdisc.org/standards/foundational/adam>, 9 pages.

cdisc.org [online], "SDTM," available on or before Nov. 21, 2021, via Internet Archive: Wayback Machine URL <https://web.archive.org/web/20211121230619/https://www.cdisc.org/standards/foundational/sdtm>, retrieved on Mar. 19, 2025, retrieved from URL <https://www.cdisc.org/standards/foundational/sdtm>, 11 pages.

phuse.s3.eu-central-1.amazonaws.com [online], "De-identification and Anonymization of Individual Patient Data in Clinical Studies—A Model Approach," 2015, retrieved on Mar. 19, 2025, retrieved from URL <https://phuse.s3.eu-central-1.amazonaws.com/Deliverables/Data+Transparency/De-identification+and+Anonymization+of+Individual+Patient+Data+in+Clinical+Studies+a+Model+Approach.pdf>, 13 pages.

Tucker et al., "Protecting patient privacy when sharing patient-level data from clinical trials," BMC Medical Research Methodology, Jul. 2016, 16(Suppl 1):77, 10 pages.

* cited by examiner

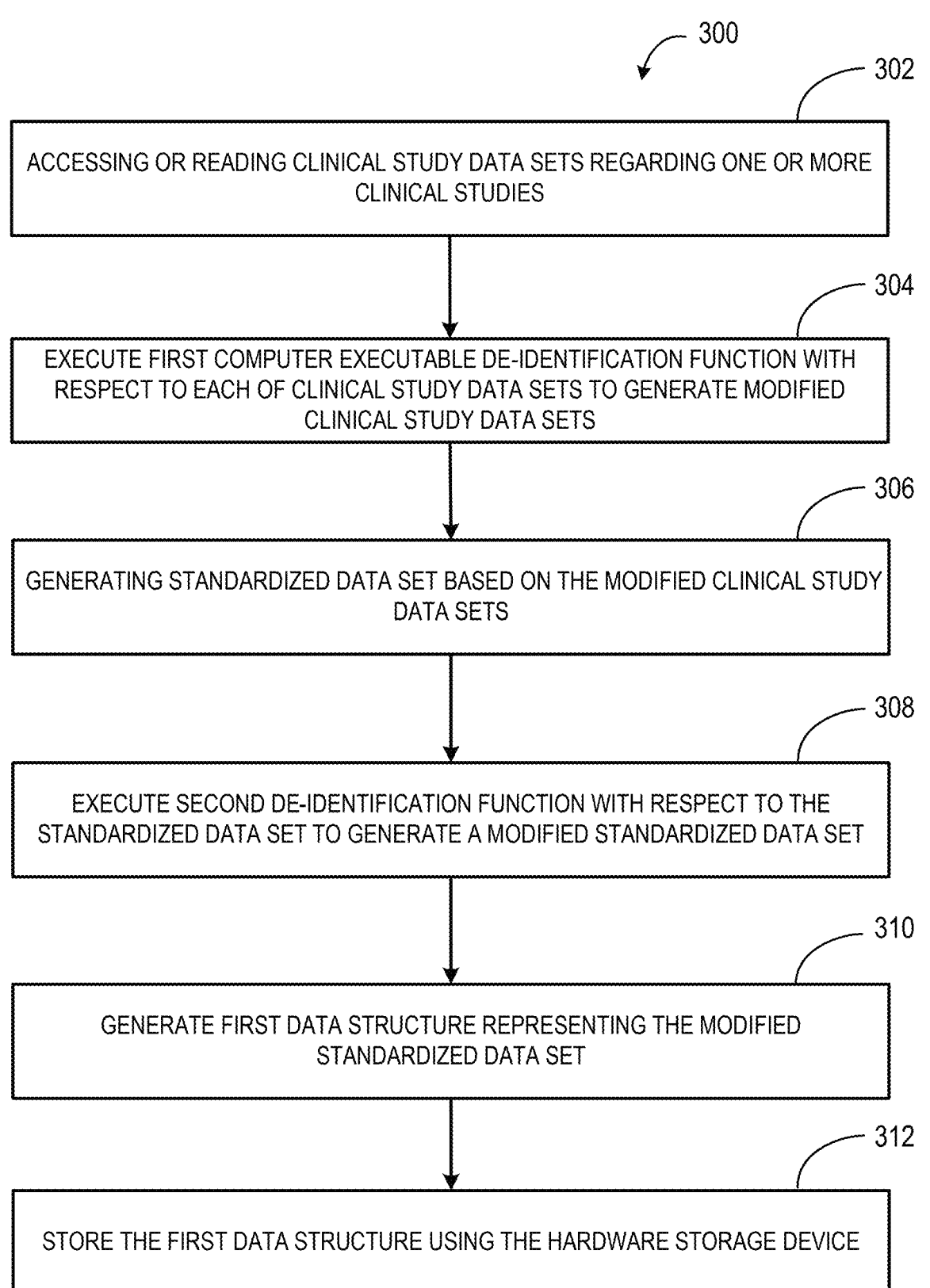

300

302

ACCESSING OR READING CLINICAL STUDY DATA SETS REGARDING ONE OR MORE CLINICAL STUDIES

304

EXECUTE FIRST COMPUTER EXECUTABLE DE-IDENTIFICATION FUNCTION WITH RESPECT TO EACH OF CLINICAL STUDY DATA SETS TO GENERATE MODIFIED CLINICAL STUDY DATA SETS

306

GENERATING STANDARDIZED DATA SET BASED ON THE MODIFIED CLINICAL STUDY DATA SETS

308

EXECUTE SECOND DE-IDENTIFICATION FUNCTION WITH RESPECT TO THE STANDARDIZED DATA SET TO GENERATE A MODIFIED STANDARDIZED DATA SET

310

GENERATE FIRST DATA STRUCTURE REPRESENTING THE MODIFIED STANDARDIZED DATA SET

312

STORE THE FIRST DATA STRUCTURE USING THE HARDWARE STORAGE DEVICE

FIG. 3

SYSTEMS AND METHODS FOR DE-IDENTIFYING HEALTHCARE DATA IN A HEALTH ANALYSIS PLATFORM

TECHNICAL FIELD

This description generally relates to systems and methods for de-identifying healthcare data in a health analysis platform by assessing and modifying physiological measurements for filtered healthcare data.

BACKGROUND

In general, maintaining privacy in healthcare data, including clinical trial data, is important for safeguarding patient information and preventing unauthorized access to sensitive data. Privacy breaches can lead to harmful consequences, including unauthorized use and distribution of personal health information. To mitigate these risks, de-identification or data masking techniques may be needed to protect and maintain privacy in the healthcare data.

SUMMARY

Implementations according to this disclosure includes a system for improving data security in a computerized health analysis platform. The system includes a hardware storage device, at least one processor, and a memory subsystem communicatively coupled to the at least one processor. The memory subsystem stores instructions which, when executed by the at least one processor, cause the at least one processor to perform operations comprising: (i) reading, from the hardware storage device, a clinical study data sets regarding one or more clinical studies; (ii) executing a first computer executable de-identification function with respect to each of the clinical study data sets to generate modified clinical study data sets; (iii) generating a standardized data set based on the modified clinical study data sets; (iv) executing a second computer-executable de-identification function with respect to the standardized data set to generate a modified standardized data set; (v) generating a first data structure representing the modified standardized data set; and (vi) storing the first data structure using the hardware storage device. Each of the clinical study data sets includes (i) one or more first data fields storing one or more first values representing identification information associated with the one or more clinical studies and entities participating in the one or more clinical studies, and (ii) one or more second data fields storing one or more second values representing clinical study information gathered during the one or more clinical studies. Executing the first computer executable de-identification function masks the one or more first values in the clinical study data sets. Executing the first computer executable de-identification function includes modifying the one or more first values in the clinical study data sets according to a first set of rules to generate a de-identified representation of the identification information. Generating the standardized data set includes: concatenating the modified clinical study data sets into the standardized data set; and at least one of: (i) remapping at least one of the first data fields in the standardized data set to a respective standardized first data field, (ii) remapping at least one of the second fields in the standardized data set to a respective standardized second data field, (iii) remapping at least one of the first values in the standardized data set to a respective standardized first value, or (iv) remapping at least one of the second values in the standardized data set to a respective standardized second value. Executing the second computer executable de-identification function masks at least one of a study design, a data collection, or treatment information of the one or more clinical studies. Executing the second computer-executable de-identification function includes modifying at least a portion of the standardized data set according to a second set of rules to generate a de-identified representation of the clinical study information.

Implementations according to this disclosure includes a method for improving data security in a computerized health analysis platform. The method includes: (i) reading clinical study data sets regarding one or more clinical studies from a hardware storage device; (ii) executing a first computer executable de-identification function with respect to direct identifiers included in each of the clinical study data sets to generate modified clinical study data sets; (iii) generating a standardized data set based on the modified clinical study data sets; (iv) executing a second computer-executable de-identification function with respect to clinical study information portion included in the standardized data set to generate a modified standardized data set; (v) generating a first data structure representing the modified standardized data set; and (vi) storing the first data structure in the hardware storage device. Each of the clinical study data sets includes (i) one or more first data fields storing one or more first values representing identification information associated with the one or more clinical studies and entities participating in the one or more clinical studies, and (ii) one or more second data fields storing one or more second values representing clinical study information gathered during the one or more clinical studies. Executing the first computer executable de-identification function masks the one or more first values in the clinical study data sets. Executing the first computer executable de-identification function includes modifying the one or more first values in the clinical study data sets according to a first set of rules to generate a de-identified representation of the identification information. Generating the standardized data set includes: concatenating the modified clinical study data sets into the standardized data set; and at least one of: (i) remapping at least one of the first data fields in the standardized data set to a respective standardized first data field, (ii) remapping at least one of the second fields in the standardized data set to a respective standardized second data field, (iii) remapping at least one of the first values in the standardized data set to a respective standardized first value, or (iv) remapping at least one of the second values in the standardized data set to a respective standardized second value. Executing the second computer executable de-identification function masks at least one of a study design, a data collection, or treatment information of the one or more clinical studies. Executing the second computer-executable de-identification function includes modifying at least a portion of the standardized data set according to a second set of rules to generate a de-identified representation of the clinical study information.

Other embodiments of this aspect include corresponding computer systems, apparatus, and computer programs recorded on one or more computer storage devices, each configured to perform the actions or operations described herein. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by a data processing apparatus, cause the apparatus to perform the actions.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 3 is a flow chart diagram of an example process for de-identifying healthcare data.

Like reference numbers and designations in the various drawings indicate like elements.

DETAILED DESCRIPTION

Figure 1:
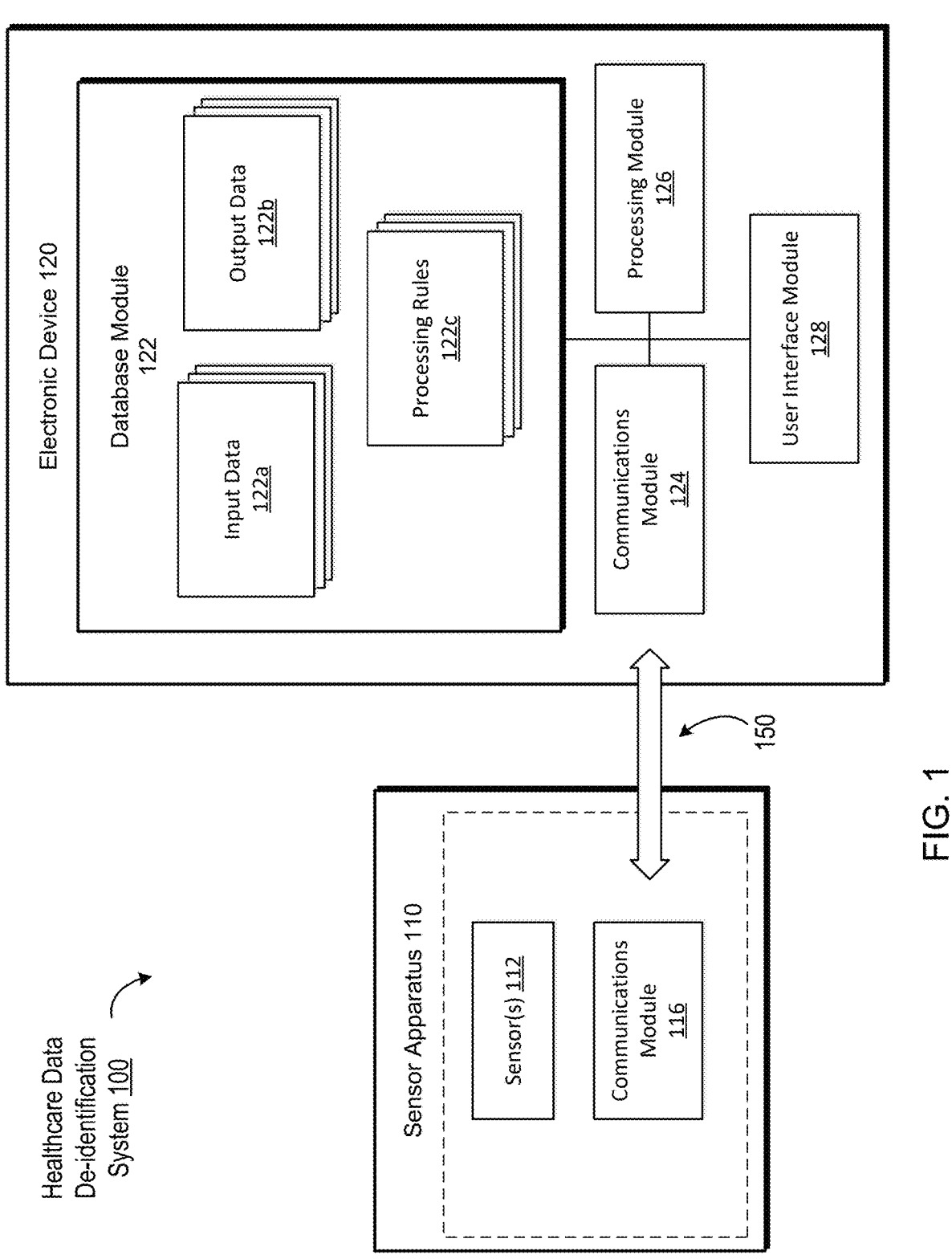
FIG. 1 is a diagram of an example of healthcare data de-identification system.

Privacy of clinical study data (e.g., clinical trial data) is important in various aspects of healthcare. For instance, privacy is essential for protecting the identification of patients. Moreover, unless protected, privacy breaches can compromise other sensitive information such as product or drug efficacy, results and data regarding the trial, entity demographics, dates of the trial, or other information pertaining to the identification of the clinical study (e.g., clinical trial). Such information can be sensitive not only for the privacy of patients but also for the relevant parties, including sponsors of the clinical study, associated with the trial.

Further, even if data pertaining to the identification of the clinical study is de-identified, it may potentially identify some of the clinical study information regarding study design, data collection, treatment information, or etc. For instance, based on study design (including treatment groups, visit schedule, dosage phase, specific time point references regarding patients being subject to the product, test, or exams), data collection (including test or examination data, biomarker, vital sign, or the like), and/or treatment information (including treatment names and treatment-related information), some of the clinical study information may potentially be identified.

Accordingly, multiple stages of anonymizing both the clinical study identification information and the clinical study information of the clinical study data can be necessary to enhance the privacy and fidelity of the clinical study data. Further, healthcare assessments, treatment decisions, or medical research relying on such clinical study data can help reduce privacy and confidentiality breaches, minimizing potential harms if the data is disclosed to the third parties or to the public.

Implementations according to this disclosure address data issues described above by at least [1] performing first de-identification operation on the healthcare data (e.g., clinical study data, real-time data, other healthcare data) by at least modifying the direct identification information portion (e.g., corresponding values in data fields) of the healthcare data according to a first set of rules, [2] generating standardized healthcare data, [3] performing second de-identification operation on the standardized healthcare data by at least modifying the clinical study information portion (e.g., corresponding values in data fields) of the standardized healthcare data according to a second set of rules.

For example, the direct identification information portion can include demographic information, identifiers associated with entities (e.g., individuals, users, patients, subjects, or the like), clinical studies, or parties associated with clinical studies, location information regarding the clinical studies, treatment information, date information associated with the clinical studies, or other direct identifiers that can be used to identify the entities, clinical studies, location, or parties associated with the clinical studies. Further, for example, the clinical study information portion can include a study design, a data collection, treatment information or information that may not directly identify the clinical study.

The direct identification information portion can be included or represented as first values in first data fields of the healthcare data. For instance, the clinical study information portion can be included or represented as second values in the second data fields of the healthcare data.

Performing the first de-identification operation can include executing a first computer executable de-identification function that can mask the first values of the first data fields of the healthcare data relating to the direct identification portion. For example, the first computer executable de-identification function can modify, based on the first set of rules, one or more of the first values associated with the direct identification information to generate a de-identified representation of the direct identification information.

Generating the standardized data set can include concatenating the modified healthcare data set (e.g., modified based on the first de-identification operation) into the standardized data set, and at least one of (i) remapping at least one of the first data fields in the standardized data set to a respective standardized first data field, (ii) remapping at least one of the second fields in the standardized data set to a respective standardized second data field, (iii) remapping at least one of the first values in the standardized data set to a respective standardized first value, or (iv) remapping at least one of the second values in the standardized data set to a respective standardized second value.

Performing the second de-identification operation can include executing a second computer-executable de-identification function with respect to the standardized data set to generate a modified standardized data set. For example, the second computer executable de-identification function can modify, based on the second set of rules, at least a portion of the standardized data set to generate a de-identified representation of the clinical study information.

For instance, the second set of rules can include rules for modifying one or more of the second values associated with the clinical study information portion.

For instance, second computer executable de-identification function can include performing data aggregation and/or data cohorting on the standardized healthcare data before and/or after modifying the portion of the standardized healthcare data based on the second set of rules.

Once the de-identification operations are complete, data structure representing the modified standardized data set can be generated. Such data structure can be stored in a data store, transmitted to a computerized health analysis platform, or output to a user interface for display.

By doing so (e.g., performing multiple stages of anonymizing both the direct identification information and the clinical study information of the healthcare data), privacy and fidelity of the clinical study data or healthcare data can be enhanced.

Further, based on enhanced privacy and fidelity of the clinical study data or healthcare data, privacy and confidentiality breaches can be reduced, thereby minimizing potential harms which might result when such data is disclosed to the unauthorized third parties or to the public.

Further, based on enhanced privacy and fidelity of the healthcare data and/or reduced privacy and confidentiality breaches, the embodiments described herein can also reduce or eliminate the expenditure of computer resources consumed in responding to potential breaches. For example, responding to breaches often requires significant CPU utilization, network bandwidth, memory, and storage resources, all of which can increase the computational load during the processing and analysis of clinical study data, healthcare data, or other data related to the breach. The embodiments described herein can prevent such breaches from occurring, thereby minimizing the computer resources (e.g., CPU utilization, memory, storage, etc.) that would otherwise be needed to address such incidents.

Further, when the data structure representing the modified standardized data set is transmitted (e.g., to a computerized health analysis platform), such data structure can be efficiently shared over a computer network with different parties who have access to it. For instance, since the first data structure includes the standardized data structure, it ensures that the data is compatible with various systems and the consistency of data processing, thus promoting more efficient and reliable data handling.

FIG. 1 shows an example of a healthcare data de-identification system 100. In particular, the healthcare data de-identification system 100 can [1] perform first de-identification operation on the healthcare data, [2] generate standardized healthcare data, and [3] perform second de-identification operation on the standardized healthcare data.

The healthcare data de-identification system 100 can include an electronic device 120 and a sensor apparatus 110 that are communicatively coupled to one another (e.g., via one or more wired or wireless communications links 150). In general, the healthcare data de-identification system 100 can access data structures (e.g., healthcare data such as clinical study data stored in a data store including database module 122 or otherwise accessible to the electronic device 120, for example, through a server) and perform de-identification of information included in such data structures through processing methods according to implementations described in this disclosure. Further, in some implementations, the healthcare data de-identification system 100 can obtain sensor data regarding a user using the sensor apparatus 110 and process the sensor data using the electronic device 120.

In general, the electronic device 120 can include any number of devices that are configured to receive, process, and transmit data. Examples of the electronic device 120 include client computing devices (e.g., desktop computers or notebook computers), server computing devices (e.g., server computers or cloud computing systems), mobile computing devices (e.g., cellular phones, smartphones, tablets, personal data assistants, notebook computers with networking capability), wearable computing devices (e.g., smart phones or headsets), and other computing devices capable of receiving, processing, and transmitting data. In some implementations, the electronic device 120 can include computing devices that operate using one or more operating systems (e.g., Microsoft Windows, Apple macOS, Linux, Unix, Google Android, and Apple IOS, among others) and one or more architectures (e.g., x86, PowerPC, and ARM, among others).

The sensor apparatus 110 includes one or more sensors 112 configured to obtain measurements regarding a physiology of the user, a behavior of the user, and/or any other characteristics of the user. For instance, the sensor apparatus 110 can include, or correspond to, a wearable device (e.g., smart watch), a smart phone, a medical monitoring system, a lab equipment, and more. As an example, the sensor apparatus can include one or more sensors 112 configured to obtain physiological parameters, including vital signs such as glucose level, heart rate, blood pressure, respiratory rate, temperature, or the like. For instance, one or more sensors can be an optical sensor (e.g., PPG), a pulse pressure sensor (PP), a pressure sensor, an electrocardiogram (ECG), bio impedance sensors, galvanic skin response sensors, tonometry/contact sensors, accelerometers, gyroscopes, pressure sensors, acoustic sensors, electro-mechanical movement sensors, and/or electromagnetic sensors. Further, for instance, when the sensor apparatus takes a form of the lab equipment, it can also measure the physiological parameters or perform blood tests, such as analyzing blood glucose levels, cholesterol, and other biomarkers.

Further, the sensor apparatus 110 includes a communications module 116 configured to transmit data and/or receive data from the electronic device 120. As an example, the communications module 116 can include one or more receivers, transmitters, and/or transceivers. In some implementations, the communications module 116 can communicate with the electronic device 120 via one or more wireless links (e.g., serial links, Ethernet links, etc.) and/or wireless links (e.g., Wi-Fi links, Bluetooth links, etc.).

In some examples, the electronic device 120 can be configured to receive sensor data (e.g., physiological parameter data such as clinical parameter(s)) obtained by the sensor apparatus 110, and process the sensor data. Further, the electronic device 120 can be configured to present information regarding the biomarkers and any other information to the user and/or another user (e.g., a health care provider).

In FIG. 1, the electronic device 120 is illustrated as a single component. However, in practice, the electronic device 120 can be implemented on one or more computing devices (e.g., each computing device including at least one processor such as a microprocessor or microcontroller). As an example, the electronic device 120 can be a single computing device, such as a single smartphone. As another example, the electronic device 120 can include multiple computing devices that are connected via a network (e.g., the Internet, local area network etc.), and the components of the electronic device 120 can be maintained and operated on some or all of the computing devices. For instance, electronic device 120 can include several computing devices, and the components of the electronic device 120 can be distributed on one or more of these computing devices.

Moreover, the electronic device 120 is illustrated as a component that is separate component from the sensor apparatus 110. However, while the electronic device 120 can be a separate component from the sensor apparatus 110, the electronic device 120 can also include, be coupled with, or be adjacent to (e.g., in a housing) the sensor apparatus 110. For example, the electronic device 120 can be a wearable device that includes, is coupled with, or is adjacent to the sensor apparatus 110.

As shown in FIG. 1, the electronic device 120 includes a database module 122, a communications module 124, a processing module 126, and a user interface module 128. The operation modules can be provided as one or more computer executable software modules, hardware modules, or a combination thereof. For example, one or more of the operation modules can be implemented as blocks of software code with instructions that cause one or more processors to execute operations described herein. In addition, or alternatively, one or more of the operations modules can be implemented in electronic circuitry such as, e.g., programmable logic circuits, field programmable logic arrays (FPGA), or application specific integrated circuits (ASIC).

The communications module 124 is configured to transmit data and/or receive data from the sensor apparatus 110. As an example, the communications module 124 can include one or more receivers, transmitters, and/or transceivers. In some implementations, the communications module 124 can communicate with the sensor apparatus 110 (e.g., via the communication module 116) via one or more wired links (e.g., serial links, Ethernet links, etc.) and/or wireless links (e.g., Wi-Fi links, Bluetooth links, etc.).

The database module 122 maintains information related to the operation of the healthcare data de-identification system 100.

As an example, the database module 122 can store input data 122a, which can include or correspond to the healthcare data that is subject to de-identification. In some implementations, the input data 122a can include at least some of the sensor data generated by the sensor apparatus 110.

As another example, the database module 122 can store output data 122b generated by electronic device 120. As an example, the output data 122b can include standardized data or de-identified data generated by the electronic device 120 based on the input data 122a.

Further, the database module 122 can store processing rules 122c specifying how data in the database module 122 can be processed to perform the operations described herein.

As an example, the processing rules 122c can include one or more rules that specify how the input data 122a is formatted, parsed, and processed to de-identify or standardize the healthcare data.

As another example, the processing rules 122c can include one or more rules that specify the conditions in which data is presented to a user (e.g., using the user interface module 128), and the manner in which the data is presented.

As another example, the processing rules 122c can include one or more rules that specify the manner in which data is stored for future retrieval and/or processing (e.g., using the database module 122).

Example data processing techniques are described in further detail below.

The processing module 126 processes data stored or otherwise accessible to the electronic device 120. For instance, the processing module 126 can be used to execute one or more of the operations described herein (e.g., by executing the processing rules 122c with respect to the input data 112a in order to generate the output data 122b).

The user interface module 128 is configured to present information to a user and/or to receive inputs from a user. As an example, the user interface module 128 can include one more display devices (e.g., display screens, touch screens, etc.) that are configured to present a user interface (e.g., graphical user interface, GUI) that enables users to interact with the electronic device 120 and/or the sensor apparatus 110. Example interactions include viewing data, transmitting data from one component to another, and/or issuing commands to the electronic device 120 and/or sensor apparatus 110. Commands can include, for example, any user instruction to one or more of the electronic device 120 and/or sensor apparatus 110 to perform particular operations or tasks. In some implementations, the user interface module can also present information to a user aurally (e.g., using one or more speakers) and/or via haptic feedback (e.g., using one more haptic generators, such as a vibration generation).

In some implementations, a software application can be used to facilitate performance of the tasks described herein. As an example, an application can be installed on the electronic device 120. Further, a user can interact with the application to input data and/or commands to the electronic device 120, and review data generated by the electronic device 120.

Figure 2:
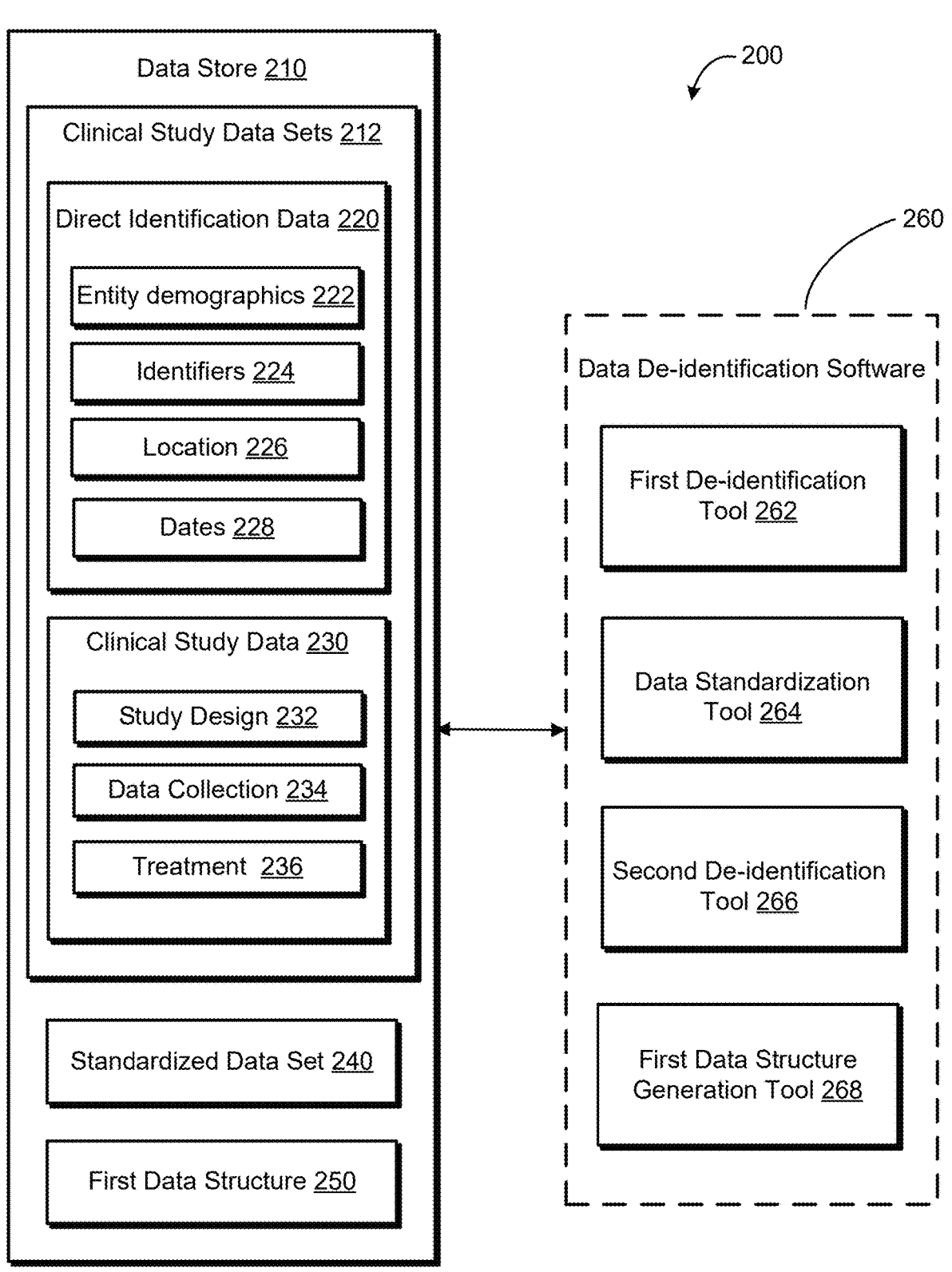
FIG. 2 is an example implementation of data de-identification software or algorithm that is utilized by an electronic device.
Figure 5:
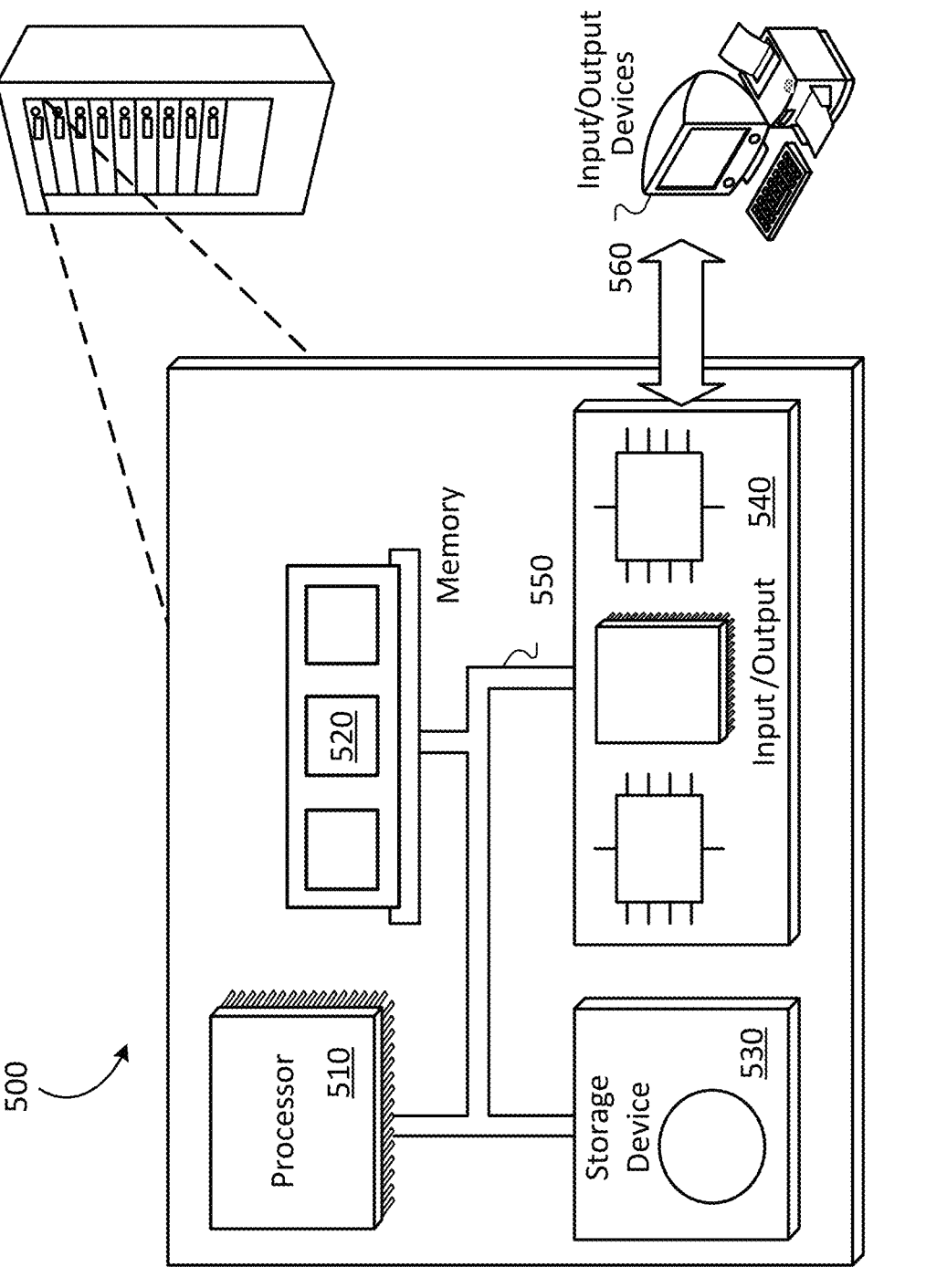
FIG. 5 is a diagram of an example computer system.

FIG. 2 is an example implementation 200 of data de-identification software or algorithm that is utilized by a processor-based electronic device (e.g., the electronic device 120 of the healthcare data de-identification system 100 of FIG. 1, a computing device (which can also be a server) of a system 500 of FIG. 5)). In particular, the software or algorithm is utilized by the electronic device to thereby [1] perform first de-identification operation on the healthcare data, [2] generate standardized healthcare data, and [3] perform second de-identification operation on the standardized healthcare data.

The example implementation 200 illustrates a data store 210 and a data de-identification software 260.

The data store 210 can include, or correspond to, a data store of the electronic device (which can also be a server). For instance, the data store 210 can be the database module 122 of the electronic device 120 and one or more storage devices 530 of the computing device (which can also be a server) of the system 500. The data store 210 can be in data communication with the electronic device (which can also be a server).

The data store 210 can include one or more of clinical study data sets 212, standardized data set 240, and first data structure 250. The clinical study data sets 212 can include direct identification data 220 and clinical study data 230.

The direct identification data 220 can include direct identifiers that can be used to identify the entities (e.g., individuals, users, patients, subjects, or the like), clinical studies, location, or parties associated with the clinical studies. For instance, for illustrative purposes, such direct identifiers can include entity demographics 222, identifiers 224 associated with one or more entities, one or more clinical studies, or one or more parties associated with the clinical studies, location information 226 regarding the clinical studies, dates 228 associated with the clinical studies, etc. Further, such direct identification data 220 can include more or less categories and/or different types of data and are not limited to above-mentioned categories of data which are also depicted in FIG. 2. The direct identification data 220 can be represented by one or more first values at (or stored in) one or more first data fields.

Such direct identification data 220 can be subject to de-identification during the first de-identification operation, as will be explained below with respect to the data de-identification software 260.

The clinical study data 230 can include information regarding study design 232, data collection 234, treatment 236, or etc. For instance, study design 232 can include treatment groups, visit schedule, dosage phase, specific time point references regarding patients being subject to the product, test, or exams, categories of tests or examinations, etc. Further, for instance, the data collection 234 can include information regarding test or examination data, biomarker, vital sign, or the like, and the treatment information can include treatment names and other treatment-related information. Further, for instance, the treatment 236 can include information regarding treatment names and treatment groups. Such study design 232, data collection 234, and treatment 236 can include more or less categories and/or different types of data, and are not limited to above-mentioned categories of data. The clinical study data 230 can be represented by one or more second values at (or stored in) one or more second data fields.

Such clinical study data 230 can be subject to de-identification during the second de-identification operation, as will be explained below with respect to the data de-identification software 260.

The clinical study data sets 212 can be used by the electronic device to generate, via the data de-identification software 260 and based on the first de-identification operation, de-identified clinical study data sets. Such de-identified clinical study data sets can also be stored in the data store 210 and be used by the electronic device to generate the standardized data set 240.

Further, the standardized data set 240 can be used by the electronic device to generate, via the data de-identification software 260 and based on the second de-identification operation, modified standardized data set. Such modified standardized data set can be used to generate the first data structure 250.

In some implementations, the clinical study data sets 212, the standardized data set 240, and the first data structure 250 can be stored in a different data store. For instance, the clinical study data sets 212 can be stored in a separate server (e.g., a computing device (which can also be a server) of the system 500), while the standardized data set 240 and/or the first data structure 250 can be stored in the data store of the electronic device (e.g., assuming that the electronic device does not take the form of server for this example), and vice versa.

Further, at least some of data de-identification and/or standardization can be implemented as respective software programs that may be executed the electronic device. A software program can include machine-readable instructions that may be stored in a memory (such as the database module 122 of FIG. 1, a memory 520, a storage device(s) 530 of FIG. 5), and that, when executed by the processor, cause the processor-based electronic device to perform the instructions of the software program. As shown, the data de-identification software 260 can include a first de-identification tool 262, a data standardization tool 264, a second de-identification tool 266, and/or a first data structure generation tool 268. In some implementations, the data de-identification software 260 can include more or fewer tools. In some implementations, some of the tools may be combined, some of the tools may be split into more tools, or a combination thereof. In some implementations, the data de-identification software 260 can be run on a server (e.g., a computing device (which can also be a server) of the system 500), or both the electronic device and the server.

In some implementations, the data standardization tool 264 and/or the first data structure generation tool 268 can take a form of a software different from the data de-identification software 260 and run on the server, while the other tools (e.g., the first de-identification tool 262, the second de-identification tool 266) can take a form of the data de-identification software 260 and run on the electronic device that is in data communication with the server, and vice versa. Further variations with respect to the first de-identification tool 262, the data standardization tool 264, the second de-identification tool 266, and the first data structure generation tool 268 being a separate software and being run on the electronic device, the server, or combination thereof, are possible.

The first de-identification tool 262 can be used to perform the first de-identification operation. For instance, the first de-identification tool 262 can include a first computer executable de-identification function with respect to each of the clinical study data sets 212 to generate modified clinical study data sets. The first computer executable de-identification function can mask the first one or more first values (or the direct identification data 220) in the clinical study data sets 212. For example, masking data, such as one or more values (e.g., the first values, the second values) can include or correspond to modifying the data by selectively obfuscating, removing, hiding, or otherwise altering a portion of the data.

For instance, executing the first computer executable de-identification function can include modifying the one or more first values in the clinical study data sets 212 according to a first set of rules to generate a de-identified representation of the direct identification data 220.

In some implementations, the first set of rules can include (i) determining that one or more first identifiers (e.g., of the identifiers 224) are associated with one or more of the entities, (ii) determining that one or more second identifiers (e.g., of the identifiers 224) are associated with the one or more parties associated with the one or more clinical studies, where the one or more parties provide at least one of the drug, the product, or the therapy used in the one or more clinical studies, (iii) removing the one or more first identifiers from the clinical study data sets, and (iv) replacing the one or more second identifiers in the clinical study data sets with one or more alphanumeric characters or symbols.

In some implementations, the first set of rules can include (i) determining that date information (e.g., the dates 228) include calendar dates, and (ii) replacing the calendar dates in the clinical study data sets (e.g., the clinical study data sets 212) with relative dates, where each of the relative dates represents a respective time offset relative to a pre-determined event. In an example, the pre-determined event can be a start date of clinical study participation of respective one or more of the entities according to the one or more clinical studies.

For example, the first set of rules can include following de-identification approaches based on certain attribute(s), as outline in below Table 1.

TABLE 1

| Attribute of Direct Identification Data | De-identification Approach |
|---|---|
| Identification Number (e.g., participant, investigator, site, laboratory) | All names and IDs are replaced with a random value |
| Names (e.g., participant, investigator, site, contractor, supplier, vendor, company staff) | Set to blank or remove all data elements except the vendor, which is grouped into a non-re-identifiable controlled vocabulary (E.g., Local/Central for identifying lab vendors). |
| Country/Region | All indications of a country/region will be represented at a granularity that has no less than 2 million individuals. |
| Investigational Product | De-identify the investigational product names in the collected data that identifies the unique sponsor trials |
| Dates | All dates in a study will be replaced by the data |

TABLE 1-continued

| Attribute of Direct Identification Data | De-identification Approach |
|---|---|
| | offset method as described below: |
| | Offset all the date values consistently by delta for a given subject |
| | Algorithm takes user input for the range of days to be used in the offset algorithm (for example, 120 to 180 days) |
| | Delta for a subject is chosen randomly from the above user provided range |
| | Partial date values are handled as below |
| | Impute the partial dates as below when day and/or month and/or year is missing |
| | Start Date Fields: missing day as 01, missing month as January and missing year as 2000 |
| | End Date Fields: missing day as last day of the month, missing month as December and missing year as 2000 |
| | Other Date Fields: missing day as 15, missing month as June and missing year as 2000 |
| | Offset the date |
| | Convert the full offset date back to the original state of partial date, i.e. remove day and/or month as required |
| Age and Date of Birth | Age Cap Rule: Exact age if ≤89 years, and set to 89 years if >89. |
| | 1. If the subject age is in the data and date of birth is not in the data, cap the age |
| | 2. If the subject age and date of birth are in the data, remove the date of birth and cap the age |
| | 3. If date of birth is in the data and age is not, follow the steps below |
| |    3.1. Calculate and store age based on date of birth and subject start date |
| |    3.2. Cap the calculated age |
| |    3.3. Remove the date of birth |
| Height and Weight | Males over 17 years old |
| | Height less than 1.53 meters, reported as ≤1.53 |
| | Height greater than 1.98 meters, reported as ≥1.98 |
| | Weight less than 45.36 kg, reported as ≤45.36 |
| | Weight greater than 181.43 kg, reported as ≥181.43 |
| | Females over 17 years old |
| | Height less than 1.42 meters, reported as ≤1.42 |
| | Height greater than 1.82 meters, reported as ≥1.82 |
| | Weight less than 40.83 kg, reported as ≤40.83 |
| | Weight greater than 158.75 kg, reported as ≥158.75 |

The data standardization tool 264 can be used to generate the standardized data set 240 based on the modified clinical study data sets (e.g., modified using the first de-identification tool 262).

For instance, generating the standardized data set 240 can include concatenating the modified clinical study data sets into the standardized data set 240, and at least one of (i) remapping at least one of the first data fields in the standardized data set 240 to a respective standardized first data field, (ii) remapping at least one of the second fields in the standardized data set 240 to a respective standardized second data field, (iii) remapping at least one of the first values in the standardized data set 240 to a respective standardized first value, or (iv) remapping at least one of the second values in the standardized data set 240 to a respective standardized second value.

The second de-identification tool 266 can be used to perform the second de-identification operation. For instance, the second de-identification tool 266 can include a second computer executable de-identification function with respect the standardized data set 240 to generate modified standardized data set. The second computer executable de-identification function can mask the one or more second values (e.g., which were carried out from the clinical study data 230 to the standardized data set 240, standardized second values that were remapped from the second values) in the standardized data set 240.

Executing the second computer executable de-identification function can include modifying at least a portion of the standardized data set 240 according to a second set of rules to generate a de-identified representation of the clinical study information. In some implementations, the second set of rules can include modifying, in the standardized data set 240, the naming conventions relating to the study design, data collection, treatment information, or other of treatment-related data. In an example, the second set of rules can include modifying, in the standardized data set 240, the naming conventions for at least one of (i) the visit information, (ii) the dosing phase, (iii) the tests or examinations, (iv) the treatment names, (v) the treatment groups, (vi) specific time point references regarding patients being subject to product, test, or examinations, or (vii) categories of tests or examinations.

The naming conventions of categories of tests or examinations can be broader and more generalized than the naming conventions of the tests or examinations. In an example, the naming convention for examinations can be specific to individual tests or assessments, while the naming convention for categories of examinations can be broader, encompassing groups of related tests or assessments.

Below Table 2 illustrates an example of modifying the naming convention of the visit information. In this example, the second values pertaining to the naming conventions of the visit schedule are modified.

TABLE 2

| Study | Original Visit Naming Convention | Final Harmonized Value |
|---|---|---|
| Study 1 | Screening | Screening and Baseline |
| Study 1 | Visit 1 | Visit 1 |
| Study 1 | Visit 2 | Visit 2 |
| Study 1 | Visit 3 | Visit 3 |
| Study 1 | Follow-up | Follow-up |
| Study 2 | Screening | Screening and Baseline |
| Study 2 | Day 1 | Visit 1 |
| Study 2 | Week 1 | Visit 2 |
| Study 2 | Week 2 | Visit 3 |
| Study 2 | Follow up | Follow-up |
| Study 3 | Screening and Baseline | Screening and Baseline |
| Study 3 | Visit 1 - Day 1 | Visit 1 |
| Study 3 | Visit 2 - Day 7 | Visit 2 |
| Study 3 | Visit 3 - Day 14 | Visit 3 |
| Study 3 | Follow-up Visit | Follow-up |

In the above example, the original visit naming convention for the visit schedule is more specific and makes it possible to identify three distinct studies in the Table 2. However, after modifying the naming convention of the visit information, it is more difficult and indeed impossible to identify three distinct studies based on the visit values.

Further, below Table 3 illustrates an example of modifying the naming convention of the dosing phase (e.g., time-point information as illustrated in Table 3). In this example, the second values pertaining to the naming conventions of the dosing phase are modified.

TABLE 3

| Study | Timepoint Naming Convention | Harmonized Value |
|---|---|---|
| Study 1 | Pre-Dose | Pre-Dose |
| Study 1 | Post-Dose | Post-Dose |

13

TABLE 3-continued

| Study | Timepoint Naming Convention | Harmonized Value |
|---|---|---|
| Study 2 | PreDose | Pre-Dose |
| Study 2 | During Dose | Concurrent Dose |
| Study 2 | Post Dose | Post-Dose |
| Study 3 | Pre-Dose | Pre-Dose |
| Study 3 | Concurrent Dose | Concurrent Dose |
| Study 3 | Post Dose | Post-Dose |

Moreover, below Table 4 illustrates an example of modifying the naming convention of the tests or examinations. In this example, the second values pertaining to the naming conventions of the tests or examinations are modified.

TABLE 4

| Study | Test Naming Convention | Harmonized Value |
|---|---|---|
| Study 1 | Rare Testing X102SFG | X102SFG Status Test |
| Study 2 | X102SFG Status Test | X102SFG Status Test |
| Study 3 | Complex X102SFG Testing | X102SFG Status Test |

In some cases, the standardized data set can include groups associated with the entities that share one or more common criteria or traits. In some implementations, executing the second computer executable de-identification function can include performing data aggregation by (i) combining the one or more second values (e.g., the second values that were carried out from the clinical study data 230 to the standardized data set 240 or standardized second values that were remapped from the second values) from two or more of the groups and (ii) generating one or more larger, less specific groups based on one or more additional common criteria or traits that are shared by the one or more larger, less specific groups. In some implementations, executing the second computer executable de-identification function can include performing data cohorting by (i) generating additional groups that exceed a number of the groups and (ii) regrouping the entities and the one or more second values in the standardized data set into the additional groups.

Once the first and second de-identification operations are completed, the first data structure generation tool 268 can generate the first data structure 250. For instance, the first data structure 250 can represent the modified standardized data set. Such data structure 250 can be stored in the data store 210, transmitted to a computerized health analysis platform, or output to a user interface for display.

Example Processes

FIG. 3 is a flow chart diagram of an example process 300 for de-identifying healthcare data. In particular, the example process 300 [1] performs first de-identification on the healthcare data, [2] generates standardized healthcare data, and [3] performs second de-identification on the standardized healthcare data. The process 300 can be implemented by a processor-based system, such as the healthcare data de-identification system 100 and a system 500, and in conjunction with the example implementation 200, as described in this disclosure.

At 302, clinical study data sets regarding one or more clinical studies are accessed or read from a hardware storage device. For instance, an electronic device (e.g., the electronic device 120 of the healthcare data de-identification system 100 or a computing device of system 500) can be used to access or read the clinical study data sets from the hardware storage device. For instance, the hardware storage device can correspond to the database module 122 of the electronic device 120 or a storage device of computing devices (e.g., one or more storage devices 530 of the computing devices of FIG. 5 that include server). In some implementations, the electronic device can correspond to a server and the hardware storage device can correspond to the server's data store.

Further, for instance, each of the clinical study data sets (e.g., the clinical study data sets 212) can include (i) one or more first data fields storing one or more first values representing identification information (e.g., information represented by the direct identification data 220) associated with the one or more clinical studies and entities participating in the one or more clinical studies, and (ii) one or more second data fields storing one or more second values representing clinical study information (e.g., information represented by the clinical study data 230) gathered during the one or more clinical studies.

In some implementations, the identification information includes at least one of (i) demographic information regarding the entities, (ii) identifiers associated with at least one of the entities, the one or more clinical studies, or one or more parties associated with the one or more clinical studies, (iii) location information regarding the one or more clinical studies, (iv) treatment information regarding at least one of a drug, a product, or a therapy used in the one or more clinical studies, or (v) date information associated with the one or more clinical studies.

In some implementations, the clinical study information includes information regarding study design, data collection, and treatment associated with the one or more clinical studies, as described above with respect to the discussion of the example implementation 200 of FIG. 2. In some implementations, at least some of the clinical study information can be represented by naming conventions for at least one of (i) visit information, (ii) dosing phase, (iii) tests or examinations, (iv) treatment names, (v) treatment groups that are associated with the plurality of entities, (vi) specific time point references regarding patients being subject to product or the test or examinations, or (vii) categories of the tests or examinations.

At 304, first computer executable de-identification function is executed with respect to each of clinical study data sets to generate modified clinical study data sets. For instance, the electronic device can be used to execute the first computer executable de-identification function on the clinical data sets.

For example, executing the first computer executable de-identification function can mask the first one or more first values in the clinical study data sets. For instance, executing the first computer executable de-identification function can include modifying the one or more first values in the clinical study data sets according to a first set of rules (e.g., the first set of rules described above with respect to the discussion of the example implementation 200 of FIG. 2) to generate a de-identified representation of the identification information.

In some implementations, the first set of rules can include replacing, in the clinical study data sets, at least one of the demographic information, the identifiers, the location information, or the treatment information with one or more alphanumeric characters or symbols.

In some implementations, the first set of rules can include (i) determining that one or more first identifiers are associated with one or more of the entities, (ii) determining that one or more second identifiers are associated with the one or more parties associated with the one or more clinical studies, where the one or more parties provide at least one of the drug, the product, or the therapy used in the one or more clinical studies, (iii) removing the one or more first identifiers from the clinical study data sets, and (iv) replacing the one or more second identifiers in the clinical study data sets with one or more alphanumeric characters or symbols.

In some implementations, the first set of rules can include (i) determining that date information includes calendar dates, and (ii) replacing the calendar dates in the clinical study data sets with relative dates, where each of the relative dates represents a respective time offset relative to a pre-determined event. In an example, the pre-determined event can be a start date of clinical study participation of respective one or more of the entities according to the one or more clinical studies.

At 306, standardized data set (e.g., the standardized data set 240) is generated based on the modified clinical study data sets. For example, the electronic device can generate the standardized data set based on the modified clinical study data sets (e.g., modified based on execution of the computer executable de-identification function).

For instance, generating the standardized data set can include concatenating the modified clinical study data sets into the standardized data set, and at least one of (i) remapping at least one of the first data fields in the standardized data set to a respective standardized first data field, (ii) remapping at least one of the second fields in the standardized data set to a respective standardized second data field, (iii) remapping at least one of the first values in the standardized data set to a respective standardized first value, or (iv) remapping at least one of the second values in the standardized data set to a respective standardized second value.

At 308, second de-identification function is executed with respect to the standardized data set to generate a modified standardized data set. For instance, the electronic device can be used to execute the second computer executable de-identification function on the standardized data set.

For example, executing the second computer executable de-identification function can mask at least one of the study design, the data collection, or the treatment information of the one or more clinical studies. For example, executing the second computer executable de-identification function can include modifying at least a portion of the standardized data set according to a second set of rules (e.g., the second set of rules described above with respect to the discussion of the example implementation 200 of FIG. 2) to generate a de-identified representation of the clinical study information.

In some implementations, the second set of rules can include modifying, in the standardized data set, the naming conventions relating to the study design, data collection, treatment information, or other of treatment-related data. In an example, the second set of rules can include modifying, in the standardized data set, the naming conventions for at least one of (i) the visit information, (ii) the dosing phase, (iii) the tests or examinations, (iv) the treatment names, (v) the treatment groups, (vi) the specific time point references regarding patients being subject to product or the test or examinations, or (vii) the categories of the tests or examinations.

In some cases, the standardized data set can include groups associated with the entities that share one or more common criteria or traits. In some implementations, executing the second computer executable de-identification function can include performing data aggregation by (i) combining the one or more second values (e.g., the second values that were carried out from the clinical study data sets to the standardized data set or standardized second values that were remapped from the second values) from two or more of the groups and (ii) generating one or more larger, less specific groups based on one or more additional common criteria or traits that are shared by the one or more larger, less specific groups. In some implementations, executing the second computer executable de-identification function can include performing data cohorting by (i) generating additional groups that exceed a number of the groups and (ii) regrouping the entities and the one or more second values in the standardized data set into the additional groups.

At 310, first data structure representing the modified standardized data set is generated. For instance, the electronic device can format the modified standardized data set data into a standardized data format suitable for storage in the hardware storage device.

At 312, the first data structure is stored in the hardware storage device. For example, the data structure can be stored in the data store (e.g., the data store 210, the database module 122 of the electronic device 120, the one or more storage devices 530, etc.).

In some implementations, in supplant of, or in addition to, storing the first data structure in the hardware storage device, the first data structure may be output to a user interface (e.g. using the user interface module 128). For example, in cases of outputting the first data structure for user display without storing the data structure, the first data structure may be generated in other format appropriate for display at step 312. For example, in cases of outputting the first data structure for user display after storing the data structure, the first data structure can be converted from the storage format to the appropriate display format, and be output.

In some implementations, the first data structure can be provided or transmitted to a computerized health analysis platform.

Figure 4:
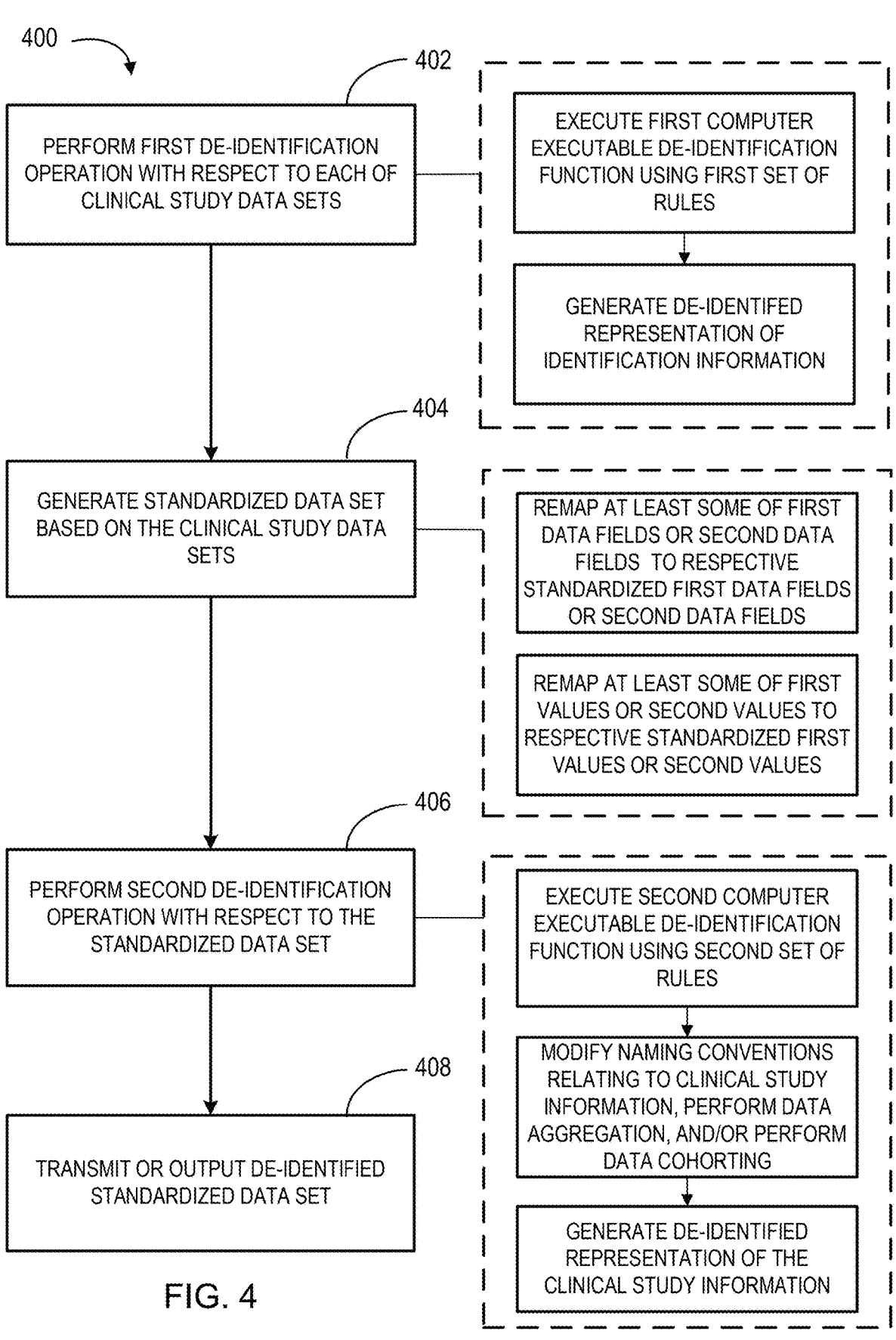
FIG. 4 is a flow chart diagram of an example process for de-identifying healthcare data.

FIG. 4 is a flow chart diagram of an example process 400 for de-identifying healthcare data. In particular, the example process 400 [1] performs first de-identification on the healthcare data, [2] generates standardized healthcare data, and [3] performs second de-identification on the standardized healthcare data. The process 400 can be implemented by a processor-based system, such as the healthcare data de-identification system 100 and a system 500, and in conjunction with the example implementation 200 and the example process 300, as described in this disclosure.

At 402, first de-identification operation is performed with respect to each of of clinical study data sets (e.g., the clinical study data sets 212). A processor-based device (e.g., the electronic device 120 of the healthcare data de-identification system 100 or a computing device of system 500) can be used to access clinical study data sets from a data store (e.g., the data store 210, the database module 122 of the electronic device 120, the one or more storage devices 530, etc.) and perform first de-identification operation with respect to each of the clinical data sets. For example, the technique regarding the first de-identification operation can be similar to the technique used in step 304 of FIG. 3.

For instance, each of the clinical study data sets (e.g., the clinical study data sets 212) can include (i) one or more first data fields storing one or more first values representing identification information (e.g., information represented by the direct identification data 220) associated with the one or more clinical studies and a plurality of entities participating in the one or more clinical studies, and (ii) one or more second data fields storing one or more second values representing clinical study information (e.g., information represented by the clinical study data 230) gathered during the one or more clinical studies.

For instance, performing the first de-identification operation with respect to each of the clinical data sets includes executing first computer executable de-identification function using a first set of rules (e.g., the first set of rules described above with respect to the discussion of the example implementation 200 of FIG. 2) to thereby generate a de-identified representation of identification information (e.g., information represented by the direct identification data 220) included in the clinical study data sets.

At 404, standardized data set is generated using the clinical study data sets which went through the first de-identification operation. The processor-based device can generate the standardized data set based on the clinical study data sets. For instance, the technique regarding the step 404 can be similar to the technique used in step 306 of FIG. 3. For example, generating the standardized data set can include concatenating the modified clinical study data sets into the standardized data set, and at least one of (i) remapping at least one of the first data fields in the standardized data set to a respective standardized first data field, (ii) remapping at least one of the second fields in the standardized data set to a respective standardized second data field, (iii) remapping at least one of the first values in the standardized data set to a respective standardized first value, or (iv) remapping at least one of the second values in the standardized data set to a respective standardized second value.

At 406, second de-identification operation is performed with respect to the standardized data set to generate a modified standardized data set. The processor-based device can perform the second de-identification operation on the standardized data set and generate the modified standardized data set. For instance, the technique regarding step 406 can be similar to the technique used in step 306 of FIG. 3.

For example, performing the second de-identification operation with respect to the standardized data set includes executing second computer executable de-identification function using a second set of rules (e.g., the second set of rules described above with respect to the discussion of the example implementation 200 of FIG. 2). For instance, executing the second computer executable de-identification includes at least one of (i) modifying naming conventions relating to the clinical study information, (ii) performing data aggregation, or (iii) performing data cohorting, as described above with respect to the example implementation 200 and the process 300 to generate a de-identified representation of the clinical study information and/or other information pertaining to the standardized data set.

At 408, after the second de-identification operation is complete, de-identified standardized data set is transmitted to a computerized health analysis platform or output to a user interface (e.g. using the user interface module 128) for display. In some implementations, the de-identified standardized data set can be stored in the data store.

Example Computer Systems

FIG. 5 depicts an example computing system, according to implementations of the present disclosure. The system 500 may be used for any of the operations discussed herein with respect to the various implementations discussed herein. The system 500 may be included in, used by, in communication with, or correspond to the electronic device 120. Further, the system 500 may include, used by, or in communication with the sensor apparatus 110. The system 500 may include one or more processors 510, a memory 520, one or more storage devices 530, and one or more input/output (I/O) devices 560 controllable through one or more I/O interfaces 540. The various components 510, 520, 530, 540, or 560 may be interconnected through at least one system bus 550, which may enable the transfer of data between the various modules and components of the system 500.

The processor(s) 510 may be configured to process instructions for execution within the system 500. The processor(s) 510 may include single-threaded processor(s), multi-threaded processor(s), or both. The processor(s) 510 may be configured to process instructions stored in the memory 520 or on the storage device(s) 530. The processor(s) 510 may include hardware-based processor(s) each including one or more cores. The processor(s) 510 may include general purpose processor(s), special purpose processor(s), or both.

The memory 520 may store information within the system 500. In some implementations, the memory 520 includes one or more computer-readable media. The memory 520 may include any number of volatile memory units, any number of non-volatile memory units, or both volatile and non-volatile memory units. The memory 520 may include read-only memory, random access memory, or both. In some examples, the memory 520 may be employed as active or physical memory by one or more executing software modules.

The storage device(s) 530 may be configured to provide (e.g., persistent) mass storage for the system 500. In some implementations, the storage device(s) 530 may include one or more computer-readable media. For example, the storage device(s) 530 may include a floppy disk device, a hard disk device, an optical disk device, or a tape device. The storage device(s) 530 may include read-only memory, random access memory, or both. The storage device(s) 530 may include one or more of an internal hard drive, an external hard drive, or a removable drive.

One or both of the memory 520 or the storage device(s) 530 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 500. In some implementations, the CRSM may include a data store that provides storage of computer-readable instructions or other information in a non-transitory format. The CRSM may be incorporated into the system 500 or may be external with respect to the system 500. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 510 and the memory 520 may be supplemented by, or incorporated into, one or more application-specific integrated circuits (ASICs).

The system 500 may include one or more I/O devices 560. The I/O device(s) 560 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 560 may also include one or more output devices such as a display, LED(s), an audio output device (e.g., a speaker), a printer, a haptic output device, and so forth. The I/O device(s) 560 may be physically incorporated in one or more computing devices of the system 500, or may be external with respect to one or more computing devices of the system 500.

The system 500 may include one or more I/O interfaces 540 to enable components or modules of the system 500 to control, interface with, or otherwise communicate with the I/O device(s) 560. The I/O interface(s) 540 may enable information to be transferred in or out of the system 500, or between components of the system 500, through serial communication, parallel communication, or other types of communication. For example, the I/O interface(s) 540 may comply with a version of the RS-232 standard for serial ports, or with a version of the IEEE 1284 standard for parallel ports. As another example, the I/O interface(s) 540 may be configured to provide a connection over Universal Serial Bus (USB) or Ethernet. In some examples, the I/O interface(s) 540 may be configured to provide a serial connection that is compliant with a version of the IEEE 1394 standard.

The I/O interface(s) 540 may also include one or more network interfaces that enable communications between computing devices in the system 500, or between the system 500 and other network-connected computing systems. The network interface(s) may include one or more network interface controllers (NICs) or other types of transceiver devices configured to send and receive communications over one or more networks using any network protocol.

Computing devices of the system 500 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 500 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device (s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

This specification uses the term "configured" in connection with systems and computer program components. For a system of one or more computers to be configured to perform particular operations or actions means that the system has installed on software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively, or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

The term "memory subsystem" can include one or more memories, where each memory may be a computer-readable medium. A memory subsystem may encompass memory hardware units (e.g., a hard drive or a disk) that store data or instructions in software form. Alternatively or in addition, the memory subsystem may include data or instructions that are hard-wired into processing circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially be claimed as such, one or more features from a claimed combination can in some cases be excised from the combination, and the claimed combination may be directed to a sub combination or variation of a sub combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A system for improving data security in a computerized health analysis platform, the system comprising:

a hardware storage device;

at least one processor; and a memory subsystem communicatively coupled to the at least one processor, the memory subsystem storing instructions which, when executed by the at least one processor, cause the at least one processor to perform operations comprising:

reading, from the hardware storage device, a plurality of clinical study data sets regarding one or more clinical studies, wherein each of the clinical study data sets comprises:

one or more first data fields storing one or more first values representing identification information associated with the one or more clinical studies and a plurality of entities participating in the one or more clinical studies, and one or more second data fields storing one or more second values representing clinical study information gathered during the one or more clinical studies;

executing a first computer executable de-identification function with respect to each of the plurality of clinical study data sets to generate a plurality of modified clinical study data sets, wherein executing the first computer executable de-identification function masks the first one or more first values in the plurality of clinical study data sets, and wherein executing the first computer executable de-identification function comprises modifying the one or more first values in the plurality of clinical study data sets according to a first set of rules to generate a de-identified representation of the identification information;

generating a standardized data set based on the plurality of modified clinical study data sets, wherein generating the standardized data set comprises:

concatenating the modified clinical study data sets into the standardized data set, and at least one of:

remapping at least one of the first data fields in the standardized data set to a respective standardized first data field, remapping at least one of the second fields in the standardized data set to a respective standardized second data field, remapping at least one of the first values in the standardized data set to a respective standardized first value, or remapping at least one of the second values in the standardized data set to a respective standardized second value;

executing a second computer-executable de-identification function with respect to the standardized data set to generate a modified standardized data set, wherein executing the second computer executable de-identification function masks at least one of a study design, a data collection, or treatment information of the one or more clinical studies, and wherein executing the second computer-executable de-identification function comprises modifying at least a portion of the standardized data set according to a second set of rules to generate a de-identified representation of the clinical study information;

generating a first data structure representing the modified standardized data set; and storing the first data structure using the hardware storage device.

2. The system of claim 1, wherein the operations comprise providing the first data structure to a computerized health analysis platform.

3. The system of claim 1, wherein the identification information comprises at least one of:

demographic information regarding the entities, identifiers associated with at least one of the entities, the one or more clinical studies, or one or more parties associated with the one or more clinical studies, location information regarding the one or more clinical studies, treatment information regarding at least one of a drug, a product, or a therapy used in the one or more clinical studies, or date information associated with the one or more clinical studies.

4. The system of claim 3, wherein the first set of rules comprises:

replacing, in the plurality of clinical study data sets, at least one of the demographic information, the identifiers, the location information, or the treatment information with one or more alphanumeric characters or symbols.

5. The system of claim 3, wherein the first set of rules comprises:

determining that one or more first identifiers are associated with one or more of the entities, determining that one or more second identifiers are associated with the one or more parties associated with the one or more clinical studies, wherein the one or more parties provide at least one of the drug, the product, or the therapy used in the one or more clinical studies, removing the one or more first identifiers from the plurality of clinical study data sets, and replacing the one or more second identifiers in the plurality of clinical study data sets with one or more alphanumeric characters or symbols.

6. The system of claim 3, wherein the first set of rules comprises:

determining that the date information comprises calendar dates, and replacing the calendar dates in the plurality of clinical study data sets with relative dates, wherein each of the relative dates represents a respective time offset relative to a pre-determined event.

7. The system of claim 6, wherein the pre-determined event corresponds to a start date of clinical study participation of a respective one of the entities according to the one or more clinical studies.

8. The system of claim 1, wherein at least some of the clinical study information is represented by naming conventions for at least one of (i) visit information, (ii) dosing phase, (iii) tests or examinations, (iv) treatment names, (v) treatment groups that are associated with the plurality of entities, (vi) specific time point references regarding patients being subject to product or the test or examinations, or (vii) categories of the tests or examinations.

9. The system of claim 8, wherein the second set of rules comprises:

modifying, in the standardized data set, the naming conventions for at least one of (i) the visit information, (ii) the dosing phase, (iii) the tests or examinations, (iv) the treatment names, (v) the treatment groups, (vi) the specific time point references regarding patients being subject to product or the test or examinations, or (vii) the categories of the tests or examinations.

10. The system of claim 1, wherein the standardized data set comprises a plurality of groups associated with (i) the plurality of entities that share one or more common criteria or traits and (ii) the one or more second values in the standardized data set, and wherein executing the computer-executable second de-identification function comprises:

performing data aggregation by (i) combining the one or more second values from two or more of the plurality of groups and (ii) generating one or more larger, less specific groups based on one or more additional common criteria or traits that are shared by the one or more larger, less specific groups.

11. The system of claim 1, wherein the standardized data set comprises a plurality of groups associated with (i) the plurality of entities that share one or more common criteria or traits and (ii) the one or more second values in the standardized data set, and wherein executing the computer-executable second de-identification function comprises:

performing data cohorting by (i) generating a plurality of additional groups that exceed a number of the plurality of groups and (ii) regrouping the plurality of entities and the one or more second values in the standardized data set into the plurality of additional groups.

12. A method comprising:

reading, by an electronic device, a plurality of clinical study data sets regarding one or more clinical studies from a hardware storage device, wherein each of the clinical study data sets comprises:

one or more first data fields storing one or more first values representing identification information associated with the one or more clinical studies and a plurality of entities participating in the one or more clinical studies, and one or more second data fields storing one or more second values representing clinical study information gathered during the one or more clinical studies;

executing, by the electronic device, a first computer executable de-identification function with respect to each of the plurality of clinical study data sets to generate a plurality of modified clinical study data sets, wherein executing the first computer executable de-identification function masks the first one or more first values in the plurality of clinical study data sets, and wherein executing the first computer executable de-identification function comprises modifying the one or more first values in the plurality of clinical study data sets according to a first set of rules to generate a de-identified representation of the identification information;

generating, by the electronic device, a standardized data set based on the plurality of modified clinical study data sets, wherein generating the standardized data set comprises:

concatenating the modified clinical study data sets into the standardized data set, and at least one of:

remapping at least one of the first data fields in the standardized data set to a respective standardized first data field, remapping at least one of the second fields in the standardized data set to a respective standardized second data field, remapping at least one of the first values in the standardized data set to a respective standardized first value, or remapping at least one of the second values in the standardized data set to a respective standardized second value;

executing, by the electronic device, a second computer-executable de-identification function with respect to the standardized data set to generate a modified standardized data set, wherein executing the second computer executable de-identification function masks at least one of a study design, a data collection, or treatment information of the one or more clinical studies, and wherein executing the second computer-executable de-identification function comprises modifying at least a portion of the standardized data set according to a second set of rules to generate a de-identified representation of the clinical study information;

generating, by the electronic device, a first data structure representing the modified standardized data set; and storing, by the electronic device, the first data structure in the hardware storage device.

13. The method of claim 12, comprising:

providing, by the electronic device, the first data structure to a computerized health analysis platform.

14. The method of claim 12, wherein the identification information comprises at least one of:

demographic information regarding the entities, identifiers associated with at least one of the entities, the one or more clinical studies, or one or more parties associated with the one or more clinical studies, location information regarding the one or more clinical studies, treatment information regarding at least one of a drug, a product, or a therapy used in the one or more clinical studies, or date information associated with the one or more clinical studies.

15. The method of claim 14, wherein the first set of rules comprises:

replacing, in the plurality of clinical study data sets, at least one of the demographic information, the identifiers, the location information, or the treatment information with one or more alphanumeric characters or symbols.

16. The method of claim 12, wherein at least some of the clinical study information is represented by naming conventions for at least one of (i) visit information, (ii) dosing phase, (iii) tests or examinations, (iv) treatment names, (v) treatment groups that are associated with the plurality of entities, (vi) specific time point references regarding patients being subject to product or the test or examinations, or (vii) categories of the tests or examinations.

17. The method of claim 16, wherein the second set of rules comprises:

modifying, in the standardized data set, the naming conventions for at least one of (i) the visit information, (ii) the dosing phase, (iii) the tests or examinations, (iv) the treatment names, (v) the treatment groups, (vi) the specific time point references regarding patients being subject to product or the test or examinations, or (vii) the categories of the tests or examinations.

18. The method of claim 12, wherein the standardized data set comprises a plurality of groups associated with (i) the plurality of entities that share one or more common criteria or traits and (ii) the one or more second values in the standardized data set, and wherein executing the computer-executable second de-identification function comprises:

performing data aggregation by (i) combining the one or more second values from two or more of the plurality of groups and (ii) generating one or more larger, less specific groups based on one or more additional common criteria or traits that are shared by the one or more larger, less specific groups.

19. The method of claim 12, wherein the standardized data set comprises a plurality of groups associated with (i) the plurality of entities that share one or more common criteria or traits and (ii) the one or more second values in the standardized data set, and wherein executing the computer-executable second de-identification function comprises:

performing data cohorting by (i) generating a plurality of additional groups that exceed a number of the plurality of groups and (ii) regrouping the plurality of entities and the one or more second values in the standardized data set into the plurality of additional groups.

20. One or more non-transitory computer-readable media storing instructions which, when executed by at least one processor, cause the at least one processor to perform;

reading a plurality of clinical study data sets regarding one or more clinical studies from a hardware storage device, wherein each of the clinical study data sets comprises:

one or more first data fields storing one or more first values representing identification information associated with the one or more clinical studies and a plurality of entities participating in the one or more clinical studies, and one or more second data fields storing one or more second values representing clinical study information gathered during the one or more clinical studies;

executing a first computer executable de-identification function with respect to each of the plurality of clinical study data sets to generate a plurality of modified clinical study data sets, wherein executing the first computer executable de-identification function masks the first one or more first values in the plurality of clinical study data sets, and wherein executing the first computer executable de-identification function comprises modifying the one or more first values in the plurality of clinical study data sets according to a first set of rules to generate a de-identified representation of the identification information;

generating a standardized data set based on the plurality of modified clinical study data sets, wherein generating the standardized data set comprises:

concatenating the modified clinical study data sets into the standardized data set, and at least one of:

remapping at least one of the first data fields in the standardized data set to a respective standardized first data field, remapping at least one of the second fields in the standardized data set to a respective standardized second data field, remapping at least one of the first values in the standardized data set to a respective standardized first value, or remapping at least one of the second values in the standardized data set to a respective standardized second value;

executing a second computer-executable de-identification function with respect to the standardized data set to generate a modified standardized data set, wherein executing the second computer executable de-identification function masks at least one of a study design, a data collection, or treatment information of the one or more clinical studies, and wherein executing the second computer-executable de-identification function comprises modifying at least a portion of the standardized data set according to a second set of rules to generate a de-identified representation of the clinical study information;

generating a first data structure representing the modified standardized data set; and storing the first data structure in the hardware storage device.

\*     \*     \*     \*     \*